United States Patent [19]

Saso

[11] Patent Number: 4,865,839

[45] Date of Patent: Sep. 12, 1989

[54] ORAL COMPOSITION CONTAINING A POLYGLYCEROL FATTY ACID MONOESTER AND AN N-ACYLAMINO ACID OR A SALT THEREOF

[75] Inventor: Kazuo Saso, Hiratsuka, Japan

[73] Assignee: Lion Corporation, Tokyo, Japan

[21] Appl. No.: 92,189

[22] Filed: Sep. 2, 1987

[30] Foreign Application Priority Data

Sep. 2, 1986 [JP] Japan .................. 61-206410

[51] Int. Cl.$^4$ ............................ A61K 7/22
[52] U.S. Cl. ........................ 424/54; 424/49
[58] Field of Search ................. 424/49, 54

[56] References Cited

U.S. PATENT DOCUMENTS 4,067,997  1/1978  Kabara .................. 424/49

OTHER PUBLICATIONS

Chem. Absts., 99, 313 (1983), Abst. No. 58900d.
Chem. Absts., 73, 228 (1970), Abst. No. 80515s.

Primary Examiner—Margaret Moskowitz
Assistant Examiner—F. T. Moezie
Attorney, Agent, or Firm—Birch, Stewart, Kolasch & Birch

[57] ABSTRACT

An oral composition containing, as a surfactant, polyglycerol fatty acid monoester having a polymerization degree of glycerol of 6 or more and 10 to 20 carbon atoms in the fatty acid moiety. An N-acylamino acid or a salt thereof may be contained in this oral composition.

8 Claims, No Drawings

ORAL COMPOSITION CONTAINING A POLYGLYCEROL FATTY ACID MONOESTER AND AN N-ACYLAMINO ACID OR A SALT THEREOF

BACKGROUND OF THE INVENTION

1. Field of the Invention

The present invention relates to an oral composition containing polyglycerol fatty acid monoester.

2. Description of the Related Art

Conventional oral compositions generally contain surfactants to increase the cleanability thereof, and the characteristics additionally required for surfactants to be used in oral compositions are an excellent formability, a good overall sensation in mouth (e.g., surfactants must not have unpleasant taste such as bitter taste, astringency, or unpleasant odor), and a high safety factor. Furthermore, a very important characteristic required for surfactants to be used in oral compositions is that the surfactants are suitable for long term storage, in that denaturing (e.g., discoloration and liquid separation) does not occur.

Anionic surfactants and nonionic surfactants are used as a surfactant in conventional oral compositions, and of these surfactants, anionic surfactants such as sodium lauryl sulfate are widely used in oral compositions because of their excellent formability. However, sodium laury sulfate has an inferior juice effect (i.e., the effect not for changing the taste of a juice after using oral compositions) and are disadvantageous in that the stable formulation of, for example, enzymes, therein is difficult. On the other hand, although nonionic surfactants are superior to anionic surfactants in, for example, safety, stabilization of effective components, and juice effect, most nonionic surfactants conventionally used in oral compositions are disadvantageous in that they have a poor foamability, taste, and odor. For example, sucrose laurate (ester) and sucrose myristate (ester) have a relatively good foamability, but have a strong bitter taste. Furthermore, when sucrose fatty acid esters are formulated into dentifrices, the dentifrices are discolored yellow and liquid separation occurs when they are stored for a long term or at an elevated temperature (e.g., at a store in the summer), and thus, are not practical.

SUMMARY OF THE INVENTION

Accordingly, the objects of the present invention are to eliminate the above-mentioned disadvantages of the prior art and to provide an oral composition containing a surfactant having a good overall sensation in mouth (e.g., foamability, taste, and odor), an excellent juice effect, a good stability, no substantial discoloration even when stored at an elevated temperature for a long time, and a high safety factor when used.

Other objects and advantages of the present invention will be apparent from the following description.

In accordance with the present invention, there is provided an aqueous oral composition containing a polyglycerol fatty acid monoester having a polymerization degree of glycerol of 6 or more and having 10 to 20 carbon atoms in the fatty acid moiety.

DESCRIPTION OF THE PREFERRED EMBODIMENTS

The present inventors have found that polyglycerol fatty acid monoesters having a polymerization degree of glycerol of 6 or more and having 10 to 20 carbon atoms in the fatty acid moiety are useful surfactants, having a high cleanability, good foamability, high safety factor, cause little irritation of the mucos membrane, can very stably formulate, for example, an enzyme, have an excellent juice effect, and an excellent overall sensation in the mouth because of a remarkably reduction of the bitter taste and astringency thereof when compared to sucrose fatty acid esters, no substantial discoloration when stored at an elevated temperature for a long time, and a good storage stability. Therefore, when these polyglycerol fatty acid monesters are formulated into oral compositions, the overall sensation in the mouth and the stability thereof are excellent, and the effective components are stably retained in the compositions. Furthermore, when N-acylamino acids or the salts thereof are used, in combination with the polyglycerol fatty acid monesters, in the oral compositions, the formability of the polyglycerol fatty acid monoesters is further increased.

According to the present invention, polyglycerol fatty acid monoesters are formulated into oral compositions such as tooth paste, powder dentifrice, liquid dentifrice, and wet dentrifrice, or a mouth wash.

The polyglycerol fatty acid monoesters usable in the present invention may be produced from glycerol and fatty acids. The polyglycerol fatty acid monoesters preferably have a glycerol polymerization degree of 6 or more, more preferably 6 to 10. When the polymerization degree of glycerol is less than 6, the foamability is poor and the monoester is not suitable for use in an oral composition.

The fatty acids for the polyglycerol fatty acid monoesters may have linear or branched acyl groups, and the carbon numbers of the acyl groups should be 10 to 20, preferably 12 to 18. When the carbon number of the acyl groups is less than 10 or more than 20, the characteristics required as surfactants for oral compositions, such as the foamability and taste, become poor and, therefore, the objects of the present invention cannot be attained. Typical examples of the acyl groups are saturated or unsaturated acyl groups such as lauroyl, myristoyl, stearoyl, and oleoyl, and these may be used alone or any mixture thereof.

According to the present invention, the monoesters of polyglycerol fatty acids should be used. Note, diesters and the like have a poor foamability and taste and, therefore, cannot attain the objects of the present invention. The terms "monoesters" used in the present invention mean those having an average degree of esterification of 1.4 or less, especially 1.3 or less.

Typical examples of the polyglycerol fatty acid monoesters are hexaglycerol monomyristate, decaglycerol monomyristate, hexaglycerol monolaurate, and decaglycerol monolaurate, hexaglycerol monostearate, and decaglycerol monooleate. These polyglycerol fatty acid monoesters may be used alone or in any mixture thereof.

The amount of the polyglycerol fatty acid monoesters to be formulated into the present oral composition is 0.5% to 5% by weight, preferably 0.5% to 3% by weight.

According to the present invention, the polyglycerol fatty acid monomers can be used alone as a surfactant in the oral composition, but other surfactants may be optionally used in addition to the polyglycerol fatty acid monoester. Examples of such other surfactants are anionic surfactants such as alkyl sulfates, olefin sulfonates, N-acylamino acids and their salts, monoglyceride sulfates, and soaps; nonionic surfactants such as fatty acid monoglycerides, fatty acid alkylolamides, polyoxyethylene sorbitan fatty acid esters, and sucrose fatty acid esters; and ampholytic surfactants. These surfactants may be used alone or in any mixture thereof.

Of these other surfactants, it is especially preferably that N-acylamino acids or their salts be used in combination with the above-mentioned polyglycerol fatty acid monoesters. Thus, when the N-acylamino acids or their salts are used in combination with the polyglycerol fatty acid monoesters, the foamability of a polyglycerol fatty acids can be further increased and oral compositions having an excellent foamability and a better overall sensation in the mouth can be provided.

The N-acylamino acids optionally usable in the present invention are those having a long-chain acyl group, especially saturated or unsaturated acyl groups having 8 to 20 carbon atoms. Typical examples of the acyl groups of such N-acylamino acids are the lauroyl group, myristoyl group, stearyl group, coconut fatty acid residues, hydrogenated tallow fatty acid residues, or residues of the mixed fatty acids mentioned above.

On the other hand, although there are no limitations to the types of the amino acids used, the use of glutamic acid, sarcosine or N-methyl-$\beta$-alanine or any mixture thereof is preferable. Typical examples of such N-acylamino acids are N-myristoyl glutamate, N-lauroyl glutamate, N-myristoyl sarcosinate, N-lauroyl sarcosinate, and N-lauroylmethyl-N-$\beta$-aranate. Furthermore, the preferable salts are sodium salts and potassium salts. When the dicarboxylic acids and the like are used as the N-acylamino acid, any monometal salts or any dimetal salts may be used as the salt as long as the salt is water-soluble.

Although there are no critical limitations to the amount of the N-acylamino acids or their salts in the present oral compositions, the preferable amount is 0.1% to 2% by weight based on the total amount of the oral composition. The amount ratio of the N-acylamino acids or their salts to the polyglycerol fatty acid monoesters is preferably 1 to 2 parts by weight of the N-acylamino acids or the salts thereof based upon 1 to 50 parts of the polyglycerol fatty acid monoesters.

The oral compositions according to the present invention may optionally contain any conventional ingredients, depending upon the types of the oral compositions. For example, dentifrices may optionally contain abrasives such as dicalcium phosphate, calcium carbonate, calcium pyrophosphate, insoluble sodium methaphosphate, and silicic anhydride; thickening agents such as glycerol, sorbitol, propylene glycol, and poyethylene glycol; binders such as carboxymethyl cellulose, carrageenan, sodium alginate, bees gum, hydroxyethyl cellulose, and polyvinyl alcohol; sweeteners such as sodium saccharin, glycyrrhizin salts, stebiocide, neohesperidyl dihydrochalcon, p-methoxycinnamic aldehyde, and perillartine; and flavors such as methanol, carvone, and anethole. Furthermore, bactericides such as fluorides (e.g., sodium monofluorophosphate, tin fluoride, and sodium fluoride) and chlorohexidine salts; phosphate compounds such as sodium phosphate; enzymes such as dextranase and amylase; anti-inflammatories such as E-aminocaproic acid, tranexamic acid, and allantoinate; and other effective components also may be optionally formulated. Also, in the case of oral clearers such as a mouth wash, various conventional ingredients may be appropriately formulated depending upon the properties of each product. According to the present invention, since the polyglycerol fatty acid monoesters substantially do not deactivate the effective components such as enzymes, these enzymes and other effective components may be formulated into the present oral composition without difficulty.

As explained above, according to the present invention, the desired oral compositions having a high safety factor, little irritation of the mucos membrane, an excellent foamability, an excellent overall sensation in the mouth (e.g., taste and odor), and good juice effects can be provided by formulating the specified polyglycerol fatty acid monoesters. Furthermore, since the present oral compositions also have an excellent storage stability, are not easily discolored even when stored for a long time, and may stably contain bactericides, enzymes, and ionic effective components such as fluorine compounds, their functions can be properly effected during application use.

EXAMPLES

The present invention will now be further illustrated by, but is by no means limited to, the following Experiments and Examples, wherein all percentages are expressed on a weight basis unless otherwise noted.

Experiment 1

The dentifrice compositions having the following formulation were prepared by using the foaming agents (i.e., surfactants) listed in Table 1. The overall sensation in the mouth and the stability of the dentifrice compositions were evaluated according to the below-mentioned standards.

The results are shown in Table 1.

|  | % |
| --- | --- |
| Dicalcium phosphate | 45.0 |
| Silica | 3.0 |
| Sodium carboxymethyl cellulose | 0.8 |
| Carrageenan | 0.2 |
| Sorbitol liquid | 26.0 |
| Propylene glycol | 3.0 |
| Sodium saccharin | 0.2 |
| Flavor | 1.0 |
| Foaming agent | 2.0 |
| Preservative | 0.1 |
| Purified water | Balance |
| Total | 100.0 |

Evaluation Standards for Foaming o: Moderate foaming
Δ: Slight foaming
x: Substantially no foaming Evaluation Standards for Taste o: Good
Δ: Slightly bitter taste
x: Strong taste, cannot be used Evaluation Standards for Stability (50° C., one month storage)

o: No discoloration
Δ: Slight discoloration
x: Strong discoloration

TABLE 1

|  |  | Foaming Agent | Overall Sensation in Mouth | | Stability Discoloration |
|---|---|---|---|---|---|
|  |  |  | Foaming | Taste |  |
| Present Invention | No. 1 | Decaglycerol monolaurate | o | o | o |
|  | No. 2 | Hexaglycerol monomyristate | o or Δ | o | o |
| Comparative | No. 3 | Decaglycerol dioleate | x | x | Δ |
|  | No. 4 | Tetraglycerol monostearate | x | o | o |
|  | No. 5 | Sucrose monolaurate | o | Δ or x | Δ or x |

Next, the dentifrice composition No. 1 (Foaming agent: decaglycerol monolaurate, present dentifrice) shown in Table 1 and the dentifrice composition No. 5 (Foaming agent: sucrose monolaurate, comparative dentifrice) shown in Table 1 were organoleptically evaluated with respect to the overall sensation in the mouth by a panel of 10 people.

The results are shown in Table 2.

TABLE 2

| Overall Sensation in Mouth | Number of Panel Members | | |
|---|---|---|---|
|  | No. 1 is better than No. 5 | No.1 and No. 5 are the same | No. 5 is better than No. 1 |
| Foamability | 3 | 5 | 2 |
| Taste | 6 | 4 | 0 |

As is clear from the results shown in Table 2, the dentifrice compositions according to the present invention containing polyglycerol fatty acid monoesters having a glycerol polymerization degree of 6 or more have an appropriate foamability and good taste, exhibit no substantial discoloration, give an excellent overall sensation in the mouth and are stabile. Furthermore, even when the denifrice composition according to the present invention is compared to that containing sucrose monolaurate, the taste of the present dentifrice is better than the dentifrice containing sucrose monolaurate, although there are no substantial differences in these dentifrice compositions.

Experiment 2

The dentifrice compositions having the same formulation as used in Experiment 1 were prepared, except that the foaming agents shown in Table 3 were used. The taste and stability (discoloration) of the dentifrice compositions were evaluated under the same evaluation standards as used in Experiment 1, and the foaming and the juice effect were evaluated according to the following evaluation standards.

The results are shown in Table 3.

Evaluation Standards for Foaming

⊚ : Good foaming
o: Appropriate foaming
Δ: Slight foaming
x: No substantial foaming Evaluation Standards for Juice Effect o: Good (Juice taste is unchanged)
x: Poor (Juice taste changed)

TABLE 3

|  |  | Foaming Agent (Formulation amount) | Overall Sensation in Mouth | | | Stability Discoloration |
|---|---|---|---|---|---|---|
|  |  |  | Foaming | Taste | Juice effect |  |
| Present Invention | No.1 | Decaglycerol monolaurate (2.0%) | o | o | o | o |
|  | No. 6 | Decaglycerol monolaurate (1.5%) + N—lauroyl sarcosinate (0.5%) | ⊚ | o | o | o |
|  | No. 7 | Decaglycerol monolaurate (1.5%) + N—hydrogenated tallow coconut oil mixed fatty acid glutamate (0.5%) | ⊚ | o | o | o |
|  | No. 8 | Decaglycerol monolaurate (1.5%) + N—lauroyl methyl-β-alanate (0.5%) | ⊚ | o | o | o |

Next, the dentifrice composition No. 1 (Foaming agent: Decaglycerol monolaurate) shown in Table 3 and the dentifrice composition No. 6 (Foaming agent: Decaglycerol monolaurate +N-lauroyl sarcosinate) shown in Table 3 were organoleptically evaluated with respect to the overall sensation in the mouth by a panel of 10 people.

The results are shown in Table 4.

TABLE 4

| Overall Sensation in Mouth | Number of Panel Members | | |
|---|---|---|---|
|  | No. 1 is better than No. 6 | Nos. 1 and 6 are the same | No. 6 is better than No. 1 |
| Foaming | 0 | 2 | 8 |
| Taste | 2 | 6 | 2 |

As is clear from the results shown in Tables 3 and 4, the dentifrice composition Nos. 6, 7, and 8 containing, as the foaming agent, both the polyglycerol fatty acid monoester and the N-acylamino acids, exhibited a remarkably excellent foamability, when compared to the dentifrice composition No. 1 containing, as the foaming agent, only the polyglycerol fatty acid monoester, although there are no substantial differences in the taste and the discoloration thereof. Furthermore, the polyglycerol fatty acid monoesters do not substantially change the juice taste and exhibit a good juice effect. Furthermore, it has also been found that, even when the N-acylamino acids are used in combination with the polyglycerol fatty acid monoesters, the juice effect is not inhibited.

Experiment 3

| Formulation | % |
| --- | --- |
| Aluminum hydroxide | 40.0 |
| Silica | 2.0 |
| Propylene glycol | 2.0 |
| Sorbitol liquid | 15.0 |
| Glycerol | 15.0 |
| Sodium alginate | 1.0 |
| Sodium saccharin | 0.2 |
| Dextranase | 5000 u/g |
| Geratin | 0.2 |
| Sodium monofluorophosphate | 0.76 |
| Decaglycerol monomyristate | 2.5 |
| Flavor | 1.0 |
| Preservative | q.s. |
| Purified water | Balance |
| Total | 100.0 |

The tooth paste prepared in the above-mentioned formulation was stored at a temperature of 40° C. for one month and the remaining activity of dextranase was evaluated thereafter.

It was found that the remaining activity of dextranase was 70% or more of the activity when prepared. Thus, it was confirmed that the formulation of the polyglycerol fatty and monoesters into the oral compositions does not inhibit but stably retains the activity of the enzyme dextranase.

Example 1: Tooth paste

| Formulation | % |
| --- | --- |
| Aluminosilicate | 20.0 |
| Glycerol | 15.0 |
| Sorbitol liquid | 40.0 |
| Polyethylene glycol #400 | 4.0 |
| Sodium carboxymethylcellulose | 1.2 |
| Sodium saccharin | 0.2 |
| Hexaglycerol monostearate | 2.0 |
| N—lauroyl glutamate | 0.5 |
| Flavor | 1.0 |
| Coloring agent | q.s. |
| Chlorohexidine gluconate | 0.01 |
| Purified water | Balance |
| Total | 100.0 |

Example 2: Tooth paste

| Formulation | % |
| --- | --- |
| Calcium carbonate (heavy) | 30.0 |
| Calcium carbonate (light) | 15.0 |
| Propylene glycol | 3.0 |
| Sorbitol liquid | 30.0 |
| Sodium carboxymethylcellulose | 1.0 |
| Sodium saccharin | 0.1 |
| Tranexamic acid | 0.1 |
| Decaglycerol monolaurate | 1.0 |
| N—lauroyl-N—methyl-β-aranate | 1.0 |
| Flavor | 1.0 |
| Preservative | q.s. |
| Purified water | Balance |
| Total | 100.0 |

Example 3: Tooth paste

| Formulation | % |
| --- | --- |
| Dicalcium phosphate | 50.0 |
| Silica | 3.0 |
| Propylene glycol | 2.0 |
| Sorbitol liquid | 25.0 |
| Sodium carboxymethylcellulose | 0.8 |
| Carrageenan | 0.3 |
| Sodium saccharin | 0.2 |
| Hexaglycerol monomyristate | 2.0 |
| Sucrose monomyristate | 1.0 |
| Allantoin chlorohydroxy aluminum | 0.1 |
| Flavor | 1.0 |
| Preservative | q.s. |
| Purified water | Balance |
| Total | 100.0 |

Example 4: Tooth paste

| Formulation | % |
| --- | --- |
| Zirconosilicate | 15.0 |
| Silica | 2.0 |
| Polyethylene glycol #400 | 3.0 |
| Sorbitol liquid | 60.0 |
| Sodium carboxymethylcellulose | 1.4 |
| Sodium saccharin | 0.2 |
| Decaglycerol monolaurate | 1.5 |
| N—myristoyl glutamate | 1.0 |
| β-Glycyrrhezinic acid | 0.01 |
| Tocopherol acetate | 0.1 |
| Sodium fluoride | 0.2 |
| Flavor | 1.0 |
| Coloring agent | q.s. |
| Purified water | Balance |
| Total | 100.0 |

Example 5: Tooth paste

| Formulation | % |
| --- | --- |
| Aluminum hydroxide | 35.0 |
| Aluminum oxide | 2.0 |
| Propylene glycol | 3.0 |
| Sorbitol liquid | 15.0 |
| Glycerol | 5.0 |
| Sodium carboxymethylcellulose | 1.2 |
| Sodium saccharin | 0.1 |
| Sodium chloride | 10.0 |
| Decaglycerol monooleate | 1.5 |
| N—myristoyl sarcosinate | 0.5 |
| Isopropylmethyl phenol | 0.05 |
| Flavor | 1.0 |
| Purified water | Balance |
| Total | 100.0 |

Example 6: Wet dentifrice

| Formulation | % |
| --- | --- |
| Dicalcium phosphate | 35.0 |
| Calcium carbonate | 40.0 |
| Glycerol | 10.0 |
| Sodium carboxymethylcellulose | 0.3 |
| Sodium saccharin | 0.2 |
| Decaglycerol monolaurate | 1.5 |
| Flavor | 1.5 |
| Purified water | Balance |
| Total | 100.0 |

Example 7: Mouth wash

| Formulation | % |
| --- | --- |
| Ethanol | 10.0 |
| Glycerol | 10.0 |
| Sorbitol liquid | 5.0 |
| Citric acid | 0.1 |
| Sodium citrate | 0.4 |
| Sodium saccharin | 0.05 |
| Hexaglycerol monolaurate | 1.5 |
| Flavor | 1.0 |
| Purified water | Balance |
| Total | 100.0 |

The oral compositions prepared in Examples 1 to 7 all gave a good overall sensation in the mouth and were stable.

I claim:

1. An oral composition containing:
   (i) a polyglycerol fatty acid monoester in an amount of 0.5% to 5% by weight of the composition having a polymerization degree of glycerol of 6 to 10 and 10 to 20 carbon atoms in the fatty acid moiety, and
   (ii) N-acylamino acid or a salt thereof, wherein said N-acylamino acid or salt thereof is used in an amount of 1 to 2 parts by weight together with 1 to 50 parts by weight of said polyglycerol fatty acid monoester, and wherein the carbon number of the acyl group in the N-acylamino acid is 8 to 20.

2. An oral composition as claimed in claim 1, wherein said amino acid is glutamic acid, sarcosine, or N-methyl-$\beta$-alanine.

3. An oral composition as claimed in claim 1, wherein the content of said N-acylamino acid or the salt thereof in the composition is 0.5 to 2% by weight.

4. An oral composition as claimed in claim 1, wherein said polyglycerol fatty acid monoester has 12 to 18 carbon atoms in the fatty acid moiety.

5. An oral composition as claimed in claim 1, wherein said polyglycerol fatty acid monoester has an average degree of esterification of 1.3 or less.

6. An oral composition as claimed in claim 1, wherein the content of the polyglycerol fatty acid monoester in the composition is 0.5% to 3% by weight.

7. An oral composition as claimed in claim 4, wherein said polyglycerol fatty acid monoester has an average degree of esterification of 1.3 or less and the content of the polyglycerol fatty acid monoester in the composition is 0.5% to 3% by weight.

8. An oral composition as claimed in claim 7, wherein the content of said N-acylamino acid or the salt thereof in the composition is 0.5 to 2% by weight.

* * * * *